United States Patent [19]

Brehm

[11] Patent Number: 5,248,709

[45] Date of Patent: Sep. 28, 1993

[54] PROCESS FOR THE AGGLOMERATION OF WATER-SWELLABLE POLYMERS BY MEANS OF SINTER GRANULATION

[75] Inventor: Helmut Brehm, Krefeld, Fed. Rep. of Germany

[73] Assignee: Chemische Fabrik Stockhausen GmbH, Krefeld, Fed. Rep. of Germany

[21] Appl. No.: 499,263

[22] PCT Filed: Dec. 1, 1988

[86] PCT No.: PCT/EP88/01089
§ 371 Date: Aug. 3, 1990
§ 102(e) Date: Aug. 3, 1990

[87] PCT Pub. No.: WO89/05326
PCT Pub. Date: Jun. 15, 1989

[30] Foreign Application Priority Data

Dec. 4, 1987 [DE] Fed. Rep. of Germany ....... 3741157

[51] Int. Cl.$^5$ .............................................. C08K 9/08
[52] U.S. Cl. .................................... 523/221; 525/221; 427/180; 427/221; 427/222; 528/502; 428/407
[58] Field of Search ............... 523/221, 111; 525/207, 525/221, 223, 230, 238, 239; 528/502; 427/180, 221, 222; 428/407

[56] References Cited

U.S. PATENT DOCUMENTS 4,190,563 2/1980 Bosley et al. .................. 523/111

FOREIGN PATENT DOCUMENTS

| 0550063 | 5/1958 | Canada | 525/207 |
| 0001706 | 5/1979 | European Pat. Off. | |
| 2064851 | 3/1987 | Japan | 525/207 |
| 2215647 | 9/1987 | Japan | 525/221 |
| 0252459 | 11/1987 | Japan | 523/111 |
| 1376091 | 12/1978 | United Kingdom | |
| 2040954 | 9/1980 | United Kingdom | |

*Primary Examiner*—Paul R. Michl
*Assistant Examiner*—Peter Szekely
*Attorney, Agent, or Firm*—Sprung Horn Kramer & Woods

[57] ABSTRACT

The present invention relates to granular materials of water-swellable polymers having a content of water-swellable polymer and agglomeration auxiliary agent as main component, and optionally further additional non-agglomerating components, the invention further relates to the method for the manufacture of said material, to its use as absorbents, and to disposable articles comprising these granular materials.

11 Claims, No Drawings

PROCESS FOR THE AGGLOMERATION OF WATER-SWELLABLE POLYMERS BY MEANS OF SINTER GRANULATION

BACKGROUND OF THE INVENTION

1. Field of the Invention

The present invention relates to granular material of water-swellable polymers, a method for the manufacture thereof and its use for the absorption of aqueous solutions, especially body liquids, such as blood and/or urine.

2. Description of Related Art

Today, water-swellable polymers are being used in various manners, particularly in the hygienic field for the absorption of body liquids, such as blood and/or urine. The water-swellable polymers must be capable to bind large amounts of liquid (water or body liquids) within a very short period of time. These known water-swellable finely divided polymers, however, tend to "block", i.e. when contacting water or aqueous solutions the outer layer of the bed becomes sticky and thus prevents the liquid from further penetrating into the innermost of the absorbent.

The water-swellable powder-like finely divided polymers are obtained in a more or less wide spectrum of grain sizes, depending on the method of manufacture, said spectrum starting from fine sizes to coarser grains up to coarse-grains. A typical grain spectrum for a water-swellable polymer ground after drying is in the range of from 10 to 800 μm, whereby the size fraction of 150 to 630 μm is used as absorbent for practical purposes. The fine powder obtained having a grain size of about 10 to 150 μm is too fine for the use as absorbent and is therefore to be regarded as waste, and, moreover, is an annoyance.

Therefore it is the object of the present invention to provide such water-swellable, powderlike polymers in a novel appearance not having the disadvantage of blocking, having the capacity of rapidly absorbing large amounts of liquids and which additionally may be produced in an easy and economical way.

SUMMARY OF THE INVENTION

According to the present invention this object is achieved by a granular material of a water-swellable polymer obtainable by agglomeration with agglomeration auxiliary substances, which, due to their ability to melt and soften, are capable of agglomerating the finely divided polymer particles.

The increase of grain size by agglomeration of finely dispersed materials is known per se. In order to build up granular material from powder particles many processes are available (Ullmann Encyclopedia of Technical Chemistry, 4th edition, vol. 18, page 157; Chem. Ind. 53 (1981), pages 37–41), said processes include sintering agglomeration and melting agglomeration. However, pelletizing of powder-like, water-swellable polymers has not been used in the art, up to now.

Surprisingly, the powdery water-swellable polymers may be agglomerated by heating mixtures having powder-like, meltable, thermoplastic and thermosetting substances as agglomeration auxiliary agents, whereby the stability of the agglomerates is increased and thus processing and use is considerably improved. Furthermore it is surprising that the granular material manufactured in this way does not tend to "block" but may absorb large amounts of liquid within a short period of time.

DESCRIPTION OF PREFERRED EMBODIMENTS

This surprising improvement of their properties can be recognized in all agglomerated water-swellable polymers, e.g., cross-linked homopolymers, copolymers and terpolymers of the acrylic and methacrylic acid, graft polymers of acryl derivatives on starch and cellulose products, polyurethanes, saponification products of cross-linked homopolymers and copolymers of the (meth)-acrylonitrile, the (meth)-acrylamide and acrylic esters, and copolymers of isobutylene and maleic acid anhydride. The polymers may contain further ionomeric and non-ionic momomers, such as, e.g., acrylamidopropanesulfonic acid, vinyl phosphonic acid, vinyl sulfonic acid, dialkylaminoalkyl(meth)-acrylates, dialkylaminoalkyl(meth)-acrylamides, quaternization products of monomers having tertiary amino groups, monomers containing one or more allyl groups, (meth)-acrylamide, alkyl(meth)-acrylamides, methylenebisacrylamide, monoacrylic-acid alkyl ester, diacrylic-acid alkyl ester, and triacrylic-acid alkyl ester, hydroxialkyl(meth)-acrylic ester, and compounds having epoxide groups. The water-swellable polymers may be present, totally or partially, as salts of ammonium, alkali or earth alkali alone or in admixture.

The manufacture of these polymers is known. They may be manufactured according to different methods: such as, e.g., solvent polymerization, precipitation polymerization, suspension polymerization, bead polymerization or graft polymerization.

Any powder-like, synthetic or natural meltable thermoplastic or thermosetting substances alone or in admixture may be used as agglomeration auxiliary agents, said substances having a melting/softening/point-/range. The following agents are meant to be examples which shall not restrict this application:

Suitable synthetic agglomeration auxiliary agents are: polyolefins and their copolymers and terpolymers, polyamides and copolyamides, polyester and copolyester, poly(meth)-acrylates and poly(meth)-nitriles and the copolymers and terpolymers thereof, polyvinyl esters and allylesters and ethers, respectively, the co-polymers and saponification products as well as actetals thereof, polyalkylene glycols, polyalkylene oxides, and polyalkoxylated compounds, PVC and the copolymers and terpolymers thereof (e.g., with vinyl acetate or maleic acid esters) and its mixtures with other polymers, polystyrene, styrene-acrylonitrile and acrylonitrile-butadiene-styrene polymers including their mixtures. Polycarbonates and polyurethanes in the form of powder are suitable, too. Furthermore, epoxide resins, aminoplasts, phenoplasts alone or in combination with a hardener may be used, too.

Natural substances, their derivatives and conversion products are excellent agglomeration powders, too, such as, cellulose ester, shellac, colophony and colophony ester and hydrogenated and disproportionated colophony, and natural thermoplastic material on the basis of hydroxybutyric acid and hydroxyvaleric acid. Further substances are the group of fatty acids and fatty acid derivatives, e.g., the esters, amides and amines of fatty acids and metallic soaps.

It is possible to add as additional non-agglomerating components separating agents such as pyrogenic $SiO_2$ (Aerosil) or $Al_2O_3$ or calcium silicate ("Silcasil") in amounts of 0.1-1%-wt of the powder mixture to be agglomerated.

The agglomeration is carried out after continuous or discontinuous admixture of the powder-like, water-swellable polymer with the powder-like agglomeration auxiliary agents by heating of the mixture. The heating is carried out in agitating or in rest position of the layer. Several methods are available for the heating or the powder mixture, e.g., by contact with the heated surfaces or hot gases, by irradiation heat, or high-frequency heating. Examples for suitable and heatable apparatuses are: tumbling mixer and force mixer, heating ovens and rotary kilns, ribbons and vibration channels, and the fluidized-bed. The necessary agglomeration temperature depends on the agglomeration auxiliary agent and theoretically ranges between temperatures of much below 0° C. up to the decomposition temperature of the water-swellable polymers. It is decisive that the agglomeration auxiliary agent and the water-swellable polymer are admixed with one another at temperatures at which both are present in the form of powders and that subsequently the agglomeration is carried out by heating of the powder mixture. The time of agglomeration depends on the time needed to heat the powder mixture, i.e., on the heat transition and the temperature difference. Times between 1 minute and 1 hour are necessary—depending on the process, temperature and layer thickness.

The course of the agglomeration may easily be observed in a heatable, transparent tumbling mixer.

The auxiliaries used for the agglomeration are powdery in the range of −100° to +300° C., preferably in the range of 20° to 200° C., and in particular in the range of 50° to 160° C., and will soften or melt above these temperatures. Thus those auxiliaries are suitable as well, which will be powdery at temperatures below said temperatures, e.g., −100° C., and, at room temperature, will e.g., be sticky. Such substances are pulverized by cold milling at low temperatures, at which they are brittle, are mixed in cold condition with the polymers and subsequently heated, e.g., to room temperature.

The amount of powdery agglomeration auxiliary agent depends on its type, grain size and the purpose of use of the granular material. The granular material may contain 75 to 99.5%-wt. of water-swellable polymer, and 25.5 to 0.5%-wt of powdery agglomeration auxiliary, respectively.

The auxiliaries used for the agglomeration may additionally contain non-agglomerating compounds such as, fillers, softeners, flow improvers, separating agents, hardeners, antistatic agents, stabilizers, and/or foaming agents.

After agglomeration, the granular material is sieved and the desired grain fraction, which may be compared to an ungranulated water-swellable polymer having the same grain size, is tested with respect to its absorption rate in a solution of sodium chloride. The oversize is ground and the undersize is returned.

The present invention further relates to disposable products for hygienic articles, like diapers and sanitary napkins comprising as absorbent for body liquids, such as water and urine, a granular material according to claim 1.

Test:

The amount of liquid absorbed is measured per gram of water-swellable polymer (granulated polymer).

The weighed amount of polymer is enclosed in a tea bag and dipped in a 0.9% sodium chloride solution. The amount of absorption is determined after
a) 15 seconds and
b) 5 minutes with subsequent centrifugation at 1400 rpm, whereby the liquid amount absorbed by the material of the tea bag is subtracted.

$$\text{Absorption amount} \left[\frac{g}{g}\right] = \frac{\text{weight after absorption [g]} - \text{weight of the tea bag [g]}}{\text{weight of the polymer [g]}}$$

It is found out that the agglomerates are considerably superior to both an non-agglomerated, water-swellable, powdery polymer of comparable grain size and the fine grain used as starting material of the agglomeration, especially with respect to the rate at which the liquid is absorbed.

Comparative polymers

Comparative polymer (commercial)

Type: cross-linked solvent polymer based on acrylic acid which is present at 70% per mole as sodium salt
grain fraction: 150-630 μm
Absorption after 15 sec: 12 g/g
Absorption after 5 min: 39 g/g

EXAMPLE 1

95 g of the comparative polymer having a grain size of smaller than 90 μm are mixed in a high-efficiency mixer for 5 minutes with 5 g copolyester having a grain size of 60-200 μm, a melting range of 115°-125° C., a melting index of 34 g/10 min. [1] and a melting viscosity of 3600 dPas at 160° C. In order to agglomerate the powder mixture is transferred into a heatable glass tumbling mixer. After 2 minutes, at a wall temperature of 160° C., the start of the agglomeration can easily be seen. 5 minutes later, the granular material is taken-off and divided into grain fractions of smaller than 150 μm, 150-630 μm, and larger than 630 μm within the air-flow classifier. The main friction of 150-630 μm is tested:

Yield of granular material: 85%
Absorption after 15 sec.: 37 g/g
Absorption after 5 min.: 41.8 g/g

EXAMPLE 2-6

Process as in example 1. The comparative polymer having a grain size of <90 μm is used for the agglomeration.

| example | amount % | Agglomeration auxiliary Name | grain-size μm | melting-range °C. | melting-index g/10 min. | conditions time min. | conditions temp. °C. | test granular mat. 150-630 μm absorption after 15 sec. g/g | absorption after 5 min. g/g |
|---|---|---|---|---|---|---|---|---|---|
| 2 | 5 | Copolyamide[4] | 0-80 | 115-125 | 15[1] | 8 | 160 | 28.8 | 41.3 |
| 3 | 5 | HD-polyethylene | 1-300 | 100-105 | 200[2] | 5 | 160 | 35.9 | 36.4 |
| 4 | 5 | Ethylene-Vinyl- | 1-300 | 70-80 | 160[1] | 10 | 160 | 23.2 | 37.2 |

|         | Agglomeration auxiliary | | | | | conditions | | test granular mat. 150-630 μm | |
|---------|---|---|---|---|---|---|---|---|---|
| example | amount % | Name | grain-size μm | melting-range °C. | melting-index g/10 min. | time min. | temp. °C. | absorption after 15 sec. g/g | absorption after 5 min. g/g |
|  |  | acetate copolymer |  |  |  |  |  |  |  |
| 5 | 5 | HD-Polyethylene | 5–74 | 109–112 | 7[3)] | 10 | 160 | 45.0 | 41.5 |
| 6 | 5 | Co-Polyamide[5)] | 0–80 | 80–90 | 65[1)] | 8 | 160 | 36.1 | 42.1 |

HD is high density
MFI is melt flow index
[1)]MFI 160° C. / 2.16
[2)]MFI 190° C. / 2.16
[3)]MFI 190° C. / 2
[4)] ®Platamid H 005, Deutsche Atochem, Bonn
[5)] ®Platamid H 103, Deutsche Atochem, Bonn

EXAMPLES 7–15

The comparative polymer having the grain size of smaller than 90 μm is admixed with the powdery agglomeration auxiliary agent, and the powder mixture is stored in the drying oven at a layer-thickness of 4 cm for a period of 30 min. After cooling, the powder cake is crushed and sieved.

EXAMPLE 17

A powder mixture of 180 g comparative polymer having a grain size of smaller than 150 μm and 20 g copolyamide powder (as in Example 6) is stored for 3 minutes in a commercial microwave oven having an connection value of 1400 watts. The final temperature is 95° C. After cooling, the powder cake is crushed and sieved.

The grain fraction 150–630 μm has an absorption rate for 0.9% sodium chloride solution of 28.5 g/g of granular material in 15 seconds.

|         | Agglomeration Auxiliary agent | | Temp. °C. | Granular material 150-630 μm Absorption after 15 sec. g/g |
|---------|---|---|---|---|
| Example | Amount % | Name |  |  |
| 7 | 5 | 90 ethylene oxide units-stearic acid | 160 | 36.1 |
| 8 | 5 | polyethylene oxide mol-wt. (number average) about 4 × 10[6] | 225 | 37.8 |
| 9 | 5 | Calcium laurate | 160 | 27.6 |
| 10 | 5 | high-press. polyethyl. | 160 | 35.9 |
| 11 | 2 | co-polyamide[1)] melting range 110–120° C. grain size up to 80 μm | 160 | 28.6 |
| 12 | 5 | " | 130 | 33.5 |
| 13 | 5 | co-polyamide[2)] melting range 115–130° C. grain size 0–80 μm | 160 | 42.5 |
| 14 | 5 | terpolymer from acrylic acid, ethylene acrylic acid ester grain size 5–74 μm MFI 190/2: 7 g/10 min density: 0.929 g/cm³ melt. range.: 98–102° C. | 130 | 29.5 |
| 15 | 5 | ethylene vinylacetate-copolymer grain size 5–74 μm MFI 190/2: 4 g/10 min melt. range: 92–95° C. | 160 | 31.5 |

[1)] ®RGriltex 1, Emser Werke AG
[2)] ®RPlatamid M 840 PA, Deutsche Atochem, Bonn, FRG.

EXAMPLE 16

A heatable screw mixer is loaded with 14.25 kg comparative polymer of the grain size of smaller than 90 μm and 0.75 kg pulverized citric-acid monohydrate. After mixing at room temperature for 10 min., the wall temperature is increased to 160° C. by heating with vapour. After 8 min., the granular material is taken off, cooled and sieved.

The grain fraction 150–630 μm has an absorption rate for 0.9% sodium chloride solution of 26 g/g in 15 seconds.

EXAMPLE 18

1.54 kg of the powder mixture as in Example 15 are put in a fluid bed. The layer height in rest position is 100 mm. At an air velocity of 0.33 m/s and an inlet air temperature of 180° C., after 28 min. The granular material yield of the grain fraction 150–630 μm is 86.5%-wt. This granular material has an absorption rate for 0.9% sodium chloride solution of 33.5 g/g of polymer in 15 seconds.

EXAMPLES 19-21

Comparative polymer of the grain size of smaller than 150 μm is admixed with the powder-like agglomeration auxiliary agent and treated in the fluidized-bed according to example 18.

| Example | Agglomeration Auxiliary Amount (%) | Agglomeration Auxiliary Name | Temp. (°C.) | Test Granular material 150–630 μm Absorption after 15 sec. (g/g) |
| --- | --- | --- | --- | --- |
| 19 | 5 | polyurethane melting range: 160–180° C. grain size: 0–500 μm Shore-A-hardness: 82 ± 2 acc. to DIN 53505 | 140 | 29.3 |
| 20 | 5 | polystyrene MFI 200/5:25 g/10 min. grain size: 5–90 μm | 160 | 25.0 |
| 21 | 5 | low pressure, low density polyethylene MFI 190/2:10 g/10 min. grain size: 5–90 μm melting range: 131–134° C. | 160 | 30.2 |

EXAMPLE 22

A powder mixture of 1455 g comparative polymer having the grain size of smaller than 100 μm, 45 g high-pressure polyethylene of the grain size 5–74 μm, the density of 0.924 g/cm³ and the melting index of 7 g/10 min (MI 190/2) and 1.5 g Aerosil 200[3]) are treated in the fluid bed until the product temperature of 140° C. is achieved. The granular material yield is:

| 16.3% of the grain size | larger than 630 μm |
| --- | --- |
| 82.2% of the grain size | 150–630 μm |
| 1.5% of the grain size | smaller than 150 μm |

The grain fraction 150–630 μm has an absorption rate of 25.4 g 0.9% sodium chloride solution per gram of granular material in 15 seconds.

3) Messrs. Degussa, FRG.

The following test is to demonstrate the surprising concentration of the sintered granular material in swollen condition. This concentration of the swollen gel is of great importance for the use of water-swellable polymers, e.g., for diapers. The higher the concentration of the gel, the lower the danger of exudation from the diapers.

The grain fraction of 200–300 μm is tested according to the Demand absorbency test, described in: "Allgemeiner Vliesstoff-Report", May 1987, pages 210–218, and the swollen gel is tested as to its concentration after reaching the maximum absorption.

5 g of max. swollen gel is put in a 10 ml pipette equipped with a piston and a 300-μm sieve which is fixed at its bottom. The pressure at which the gel is pressed through the openings of the sieve is determined under increasing weight load of the piston. The load on the piston of the pipette is expressed in g per cm².

| Product acc. Example No. | Max. Amount of Liquid absorbed ml/g | Load g/cm² |
| --- | --- | --- |
| comparative polymer | 67 | 700 |
| 5 | 56 | 900 |
| 14 | 55.1 | 1060 |
| 15 | 57 | 760 |

I claim:

1. A process for the manufacture of granular material which comprises
   a) mixing water-swellable polymer particles of from 10 to 150 μm with an agglomeration auxiliary agent which is powdery in the range of −100° to +300° C., the water-swellable polymer particles being present in from 75 to 99.5% by weight and the agglomeration auxiliary agent particles being present in from 25 to 0.5% by weight,
   b) heating the mixture for a time between one minute and one hour sufficient to render the auxiliary agent particles adhesive, thereby agglomerating at least about 85% by weight of the water-swellable polymer particles into particles of about 150 to 630 μm,
   c) cooling, and
   d) optionally classifying the granular material substantially to remove therefrom particles outside the range of about 150 to 630 μm.

2. A process according to claim 1, wherein the agglomeration auxiliary agent has a melting/softening point temperature range.

3. A process according to claim 1, wherein the auxiliary agglomerating agent comprises at least one of a polyolefin, polyamide, polyester, poly(meth)-acrylate, poly(meth)-acrylonitrile, polyalkylene oxide, polyvinylchloride, polystyrene, polycarbonate or polyurethane.

4. A process according to claim 1, wherein the auxiliary agent comprises at least one of an epoxide resin, aminoplast or phenoplast, optionally in combination with a hardener.

5. A process according to claim 1, wherein the auxiliary agent comprises at least one of a cellulose ester, shellac, colophony or derivative thereof, or a natural thermoplast based on a fatty acid or derivative thereof.

6. A process according to claim 1, wherein there is additionally included in the materials being heated at least one of a non-agglomerating filler, softener, flow improving agent, separating agent, hardener, antistatic agent, stabilizer or foaming agent.

7. A process according to claim 1, wherein the water-swellable polymer comprises at least one of a polymer of (meth)-acrylic acid, a polymer of at least partially saponified (meth)-acrylonitrile, a polymer of at least partially saponified (meth)-acrylamide, a polymer of an at least partially saponified (meth)-acrylic acid ester, a graft copolymer of (meth)-acrylonitrile or (meth)-acrylamide with starch or cellulose or a derivative thereof, a polyurethane and a polymer of isobutylene and maleic acid anhydride.

8. A process according to claim 1, wherein the water-swellable polymer comprises an ionogenic or non-ionic monomer.

9. A process according to claim 1, wherein the water-swellable polymer is present at least partially as an ammonium, alkali or alkaline earth metal salt.

10. Granular particles produced by the process of claim 1.

11. Granular material of water-swellable polymers according to claim 10 at least 85% of which is from 150 to 630 μm in size, characterized by a content of water-swellable polymer of 75 to 99.5%-wt, and 25 to 0.5%-wt of an agglomeration auxiliary agent as main component, which agglomeration auxiliary agent is a powder and is capable of agglomerating the finely divided water-swellable polymer particles to particle sizes which can be used as absorbent for practical purposes, and optionally further additional non-agglomerating components.

* * * * *